United States Patent
Maguire et al.

(10) Patent No.: US 11,381,650 B2
(45) Date of Patent: Jul. 5, 2022

(54) SYSTEM AND SERVER FOR ANALYZING AND INTEGRATING DATA COLLECTED BY AN ELECTRONIC DEVICE

(71) Applicant: Knowmadics, Inc., Herndon, VA (US)

(72) Inventors: Paul Maguire, Manassas, VA (US); Lisa Cinnamon, Hammonds Plain (CA); Claire Ostrum, Leesburg, VA (US); Brian O'Toole, McLean, VA (US); Steven Edgett, Kanata (CA); Charles Corcoran, Duluth, GA (US)

(73) Assignee: KNOWMADICS, INC., Herndon, VA (US)

( * ) Notice: Subject to any disclaimer, the term of this patent is extended or adjusted under 35 U.S.C. 154(b) by 339 days.

(21) Appl. No.: 15/691,785

(22) Filed: Aug. 31, 2017

(65) Prior Publication Data

US 2017/0366629 A1 Dec. 21, 2017

Related U.S. Application Data

(63) Continuation of application No. 14/561,564, filed on Dec. 5, 2014, now Pat. No. 9,807,183.
(Continued)

(51) Int. Cl.
*H04L 67/50* (2022.01)
*H04L 67/125* (2022.01)
(Continued)

(52) U.S. Cl.
CPC .............. *H04L 67/22* (2013.01); *G16H 50/80* (2018.01); *H04L 67/125* (2013.01); *H04L 67/36* (2013.01); *H04W 4/02* (2013.01)

(58) Field of Classification Search
CPC ....... H04L 67/22; H04L 67/125; H04L 67/36; G16H 50/80
See application file for complete search history.

(56) References Cited

U.S. PATENT DOCUMENTS 6,839,552 B1 1/2005 Martin
7,058,710 B2 6/2006 McCall et al.
(Continued)

FOREIGN PATENT DOCUMENTS

GB 2401752 11/2004
GB 2401752 A * 11/2004 ........ H04M 1/72538

OTHER PUBLICATIONS

Maguire et al., U.S. Appl. No. 14/561,564, filed Dec. 5, 2014, entitled "Crowd-Sourced Computer-Implemented Methods and Systems of Collecting and Transforming Portable Device Data" (parent application).
(Continued)

*Primary Examiner* — Tauqir Hussain
(74) *Attorney, Agent, or Firm* — Nixon & Vanderhye, P.C.

(57) ABSTRACT

A system for analyzing data received from at least one mobile electronic device comprises a mobile electronic device and a server. The mobile electronic device includes a sensor configured to collect video, audio and/or imagery data, and the mobile electronic device is configured to initiate collection of data based on a command from a user of the mobile electronic device. The server includes a receiver configured to receive the video, audio and/or imagery data collected by the sensor of the mobile electronic device and a processing system. The processing system of the server includes a processor and is configured to, when a condition is met in accordance with a rule established on the server, issue a command to turn on the sensor of the mobile electronic device and enable the mobile electronic device to transmit the video, audio and/or imagery data collected by the sensor to the server, without any input by the user of the mobile electronic device. In addition, the video, audio
(Continued)

and/or imagery data are collected by the sensor at a location of the mobile electronic device.

17 Claims, 16 Drawing Sheets

Related U.S. Application Data

(60) Provisional application No. 61/914,755, filed on Dec. 11, 2013, provisional application No. 61/912,944, filed on Dec. 6, 2013, provisional application No. 61/912,337, filed on Dec. 5, 2013.

(51) Int. Cl.
*H04L 67/75* (2022.01)
*H04W 4/02* (2018.01)
*G16H 50/80* (2018.01)

(56) References Cited

U.S. PATENT DOCUMENTS

| | | | |
|---|---|---|---|
| 7,406,507 B2 | 7/2008 | Piccioni | |
| 7,822,848 B2 | 10/2010 | Muller | |
| 7,860,222 B1 | 12/2010 | Sidler et al. | |
| 7,873,349 B1 | 1/2011 | Smith | |
| 7,924,149 B2 | 4/2011 | Mendelson | |
| 8,024,330 B1 | 9/2011 | Franco et al. | |
| 8,045,954 B2 | 10/2011 | Barbeau et al. | |
| 8,165,560 B2 | 4/2012 | Stenquist | |
| 8,265,597 B2 | 9/2012 | Smith | |
| 8,311,513 B1* | 11/2012 | Nasserbakht | H04L 63/0853 455/457 |
| 8,311,515 B1 | 11/2012 | Smith | |
| 8,314,683 B2 | 11/2012 | Pfeffer | |
| 8,457,596 B2 | 6/2013 | Smith | |
| 8,606,230 B2 | 12/2013 | Smith | |
| 8,862,092 B2 | 10/2014 | Reitnour | |
| 9,000,933 B2 | 4/2015 | Ray et al. | |
| 9,014,660 B2 | 4/2015 | Pahlevani | |
| 9,294,900 B2 | 3/2016 | Pahlevani | |
| 2005/0085257 A1* | 4/2005 | Laird | A61B 5/1117 455/404.1 |
| 2006/0015254 A1 | 1/2006 | Smith | |
| 2006/0168185 A1 | 7/2006 | McCall et al. | |
| 2007/0035612 A1 | 2/2007 | Korneluk et al. | |
| 2007/0218900 A1 | 9/2007 | Abhyanker | |
| 2007/0294177 A1 | 12/2007 | Volk | |
| 2008/0068130 A1 | 3/2008 | Batta | |
| 2008/0077458 A1 | 3/2008 | Andersen | |
| 2008/0189162 A1* | 8/2008 | Ganong | G06F 16/958 701/300 |
| 2008/0208962 A1 | 8/2008 | Kim et al. | |
| 2009/0005068 A1 | 1/2009 | Forstall | |
| 2009/0047972 A1* | 2/2009 | Neeraj | H04W 4/185 455/456.1 |
| 2009/0281850 A1 | 11/2009 | Bruce | |
| 2009/0323953 A1* | 12/2009 | Narayan | H04L 67/2804 380/258 |
| 2009/0326381 A1 | 12/2009 | Yuan | |
| 2010/0007487 A1* | 1/2010 | Warner | G08B 27/006 455/404.1 |
| 2010/0324936 A1* | 12/2010 | Vishnubhatla | G06Q 50/22 715/810 |
| 2011/0130636 A1 | 6/2011 | Daniel et al. | |
| 2011/0217958 A1 | 9/2011 | Kiesel | |
| 2011/0225198 A1 | 9/2011 | Edwards et al. | |
| 2011/0319051 A1 | 12/2011 | Reitnour | |
| 2012/0021770 A1* | 1/2012 | Naqvi | G06Q 30/0631 455/456.3 |
| 2012/0290665 A1* | 11/2012 | Pickering | G06Q 10/107 709/206 |
| 2012/0296559 A1* | 11/2012 | Gueziec | G08G 1/096775 701/117 |
| 2013/0046847 A1* | 2/2013 | Zavesky | G06Q 30/0261 709/217 |
| 2013/0084882 A1 | 4/2013 | Khorashadi | |
| 2013/0124244 A1* | 5/2013 | Johnson | G06Q 10/101 705/7.12 |
| 2013/0157612 A1 | 6/2013 | Cordero | |
| 2013/0183924 A1 | 7/2013 | Saigh | |
| 2013/0190008 A1* | 7/2013 | Vathsangam | G06V 40/25 455/456.1 |
| 2013/0231851 A1* | 9/2013 | Chen | G08G 1/012 701/119 |
| 2013/0329047 A1* | 12/2013 | Jankowski | H04W 4/029 348/158 |
| 2014/0099998 A1 | 4/2014 | Smith | |
| 2014/0253326 A1* | 9/2014 | Cho | G08B 25/10 340/539.11 |
| 2015/0039415 A1* | 2/2015 | Boldyrev | G06Q 30/00 705/14.41 |
| 2015/0052485 A1 | 2/2015 | Grounds | |
| 2015/0137967 A1* | 5/2015 | Wedig | G08B 25/016 340/501 |
| 2015/0181372 A1* | 6/2015 | Huang | H04W 4/029 455/456.1 |
| 2015/0199895 A1* | 7/2015 | Hilliges | G08G 1/205 340/425.5 |
| 2015/0227999 A1 | 8/2015 | Maguire et al. | |
| 2015/0358796 A1* | 12/2015 | Sarna, II | H04W 4/023 455/404.1 |
| 2016/0182707 A1* | 6/2016 | Gabel | G06Q 10/10 455/404.2 |
| 2016/0183074 A1 | 6/2016 | Pahlevani | |

OTHER PUBLICATIONS

Candy Castle—A prototype for Pervasive Health Games, Christopher Stach, PerCom Demos 2012, Lugano (Mar. 20, 2012), pp. 501-203.
File history of the Re-Examination of U.S. Pat. No. 8,265,597—Reexamination Control No. U.S. Appl. No. 90/013,020, filed Oct. 8, 2013.
Mobile Phones as Computing Devices: "The Viruses are Coming!" by David Dagon, Tom Martin, and Thad Stamer, published in *Pervasive Computing*, published by the IEEE CS and IEEE ComSoc, 2004.
"How To Tell If Your Cell Phone Is Bugged" by Lauren Weinstein (Vortex Technology), published as http://lauren.vortex.com/archive/000202.html; Dated Dec. 3, 2006.
"FlexiSPY Pro-X, FlexiSPY" [online], published Apr. 24, 2008 [retrieved on Sep. 2, 2013]. Retrieved from the Intenet:<URL: http://wayback.archive.org/web/20080409170704/http://www.flexispy.com/faq.htrn#03.> (and linked pages).
"*Fake Shutdown* 1.0", NONAGS [online] published Nov. 12, 2001 [retrieved on Sep. 6, 2013]. Retrieved from the internet <URL: http://www.nonags.com/freeware-fake-shutdown 969.html>.
"Stealthy Video Capturer: A New Video-based Spyware in 3G Smartphones" by Nan Xu et al., Source: Proceedings of the Second ACM Conference on Wireless Network Security, pp. 69-78, 2009.
FBI Taps Cell Phonemic As Eavesdropping Tool; by Declan McCullagh; Conet News, Source: http://news.cnet.com/2100-1029-6140191.html; Dated Dec. 1, 2006.
Muller, Michael, et al., "MoCoMapps—An Experiment in Crowdsourcing both Data and Applications for Mobile Services," CHI 2011 Workshop, Data Collection: By the people, for the people, Vancouver, BC, (4 pages) Canada, May 2011. http://129.34.20.8/cambridge/Technical_Reports/2011/MoCoMapps%20-%20muller%20TR.pdf (4 pages).
Wang, Tengda, "The Collection of Information for Emergency Management: An iPhone Client with Web Service," Masters Project for Department of Computing Studies and Technology, Available (Expected Completion: Summer 2011), http://quav.poly.asu.edu/Lindquist/Students/pubs/TengdaWangReport.pdf. (8 pages).
Wu, Anna, et al., "Geo-Tagged Mobile Photo Sharing in Collaborative Emergency Management," VINCI 2011, Aug. 4-5, 2011, ACM, 2011 (8 pages).

(56) References Cited

OTHER PUBLICATIONS

Richmond, Riva, "An App for Reporting an Emergency," Gadgetwise Blog, The New York Times, Jul. 19, 2011 (3 pages).
ELERTS iTunes Preview, App Store, Captured by Internet Archive Wayback Machine on Oct. 24, 2011.
ELERTS Corporation, Home Page, Captured by Internet Archive Wayback Machine on Jan. 28, 2011.
"How ELERTS Works," Captured by Internet Archive Wayback Machine on Sep. 2, 2011.
Shi, Jeffery, "Location Based Citizen Reporting: A Case Study of a Road Hazard Reporting System," SDM Thesis, Massachusetts Institute of Technology, May 2009 (83 pages).

\* cited by examiner

FIG. 3

- SilverEye allows you to import the CASES data and to map it like any other sensor

- SilverEye integrates the CASES data with other sensor feeds

SYSTEM AND SERVER FOR ANALYZING AND INTEGRATING DATA COLLECTED BY AN ELECTRONIC DEVICE

CROSS-REFERENCE TO RELATED APPLICATIONS

This application is a continuation of application Ser. No. 14/561,564, filed Dec. 5, 2014, which claims priority under 35 U.S.C. § 119(e) to U.S. Application No. 61/912,337, filed Dec. 5, 2013, U.S. Application No. 61/912,944, filed Dec. 6, 2013, and U.S. Application No. 61/914,755, filed Dec. 11, 2013, the entire content of each of which is incorporated into the present application by reference.

COPYRIGHT

A portion of the disclosure of this patent document contains material which is subject to copyright protection. The copyright owner has no objection to the facsimile reproduction by anyone of the patent disclosure, as it appears in the Patent and Trademark Office patent files or records, but otherwise reserves all copyright rights whatsoever.

FIELD OF THE INVENTION

One aspect of the present disclosure relates to crowd sourced computer-implemented methods and systems of collecting and transforming portable device data to cause actionable responses including machine to machine (M2M) such as computer aided dispatch (CAD), analytic tools, or command and control (C2) tools; and/or machine to person (M2P) by one or more human actors, such as an emergency first responder, a crime investigation organization, public safety personnel, a private citizen, or a private security firm.

Another aspect of the present disclosure relates to crowd sourced computer-implemented methods and systems of collecting and transforming portable device data computer-implemented methods and systems for communicating data to cause actionable responses including machine to machine (M2M) such as computer aided dispatch (CAD), analytic tools, or command and control tools; and/or machine to person (M2P) to cause actionable responses by one or more human actors, such as public health actors.

BACKGROUND OF THE INVENTION

Prior art systems in many cases require other specialized pieces of hardware in addition to the portable device and/or require there to be person in the loop that makes judgments about the data being received. Additionally many of those other systems merely receive alerts or updates from some other sources of data or send a picture or text to a 3rd party to create an alert. Other apps like the WAZE application (hereinafter "app") are used in a crowd-sourced fashion to avoid public safety personnel (e.g., circumvent traffic cameras, radar checks, etc.) or to get basic situational awareness.

However, the WAZE app simply sends data collected by users to a public website for viewing by other users. The WAZE app does not include any features where a server analyzes the data and sends specific alerts/commands to individual users to create enhanced situational awareness and/or to provide instructions.

Further, there exists a need to generate public health data by and from the public to the public in a time-sensitive fashion. Crowd-sourced Apps and services PatientsLikeMe, and 23 and Me focus on serving individuals in a peer-to-peer way but they do not serve the larger public good in a many-to-many or one-to-many manner. The World Health Organization (WHO) and the Center for Disease Control (CDC) all publish warnings and bulletins but all based on scientific field collected data not near-real-time crowd sourced data that can be updated by users continuously.

SUMMARY OF THE INVENTION

The present invention broadly comprises crowd-sourced computer-implemented methods and systems of collecting and transforming portable device data. One embodiment of the invention may be implemented as a system including an electronic device including a sensor configured to collect data, the device configured to begin collection of data based on a command from a user of the electronic device; and a server configured to issue a command to the electronic device to turn on the sensor and transmit data collected by the sensor to the server without any input by the user of the electronic device when a condition is met.

Another aspect may be embodied as a system including an electronic device configured to collect data using a sensor; and a server configured to receive data from the electronic device, to create a map using the data, and to transmit the map to the electronic device.

Still another aspect may be embodied as a system including an electronic device configured to collect data using a sensor; and a server configured to receive the data from the electronic device, to create a map using the data, and to transmit warning information to the electronic device.

BRIEF DESCRIPTION OF THE DRAWINGS

A full and enabling disclosure of the present subject matter, including the best mode thereof, directed to one of ordinary skill in the art, is set forth in the specification, which makes reference to the appended figures, in which:

FIGS. 3 and 4 illustrate exemplary screen shots for a client device which may be part of the exemplary systems shown in FIGS. 1 and 2;

DETAILED DESCRIPTION OF THE PREFERRED EMBODIMENTS

Reference is presently made in detail to exemplary embodiments of the present subject matter, one or more examples of which are illustrated in or represented by the drawings. Each example is provided by way of explanation of the present subject matter, not limitation of the present subject matter. In fact, it will be apparent to those skilled in the art that various modifications and variations can be made in the present subject matter without departing from the scope or spirit of the present subject matter. For instance, features illustrated or described as part of one embodiment can be used with another embodiment to yield a still further embodiment. Thus, it is intended that the present subject matter covers such modifications and variations as come within the scope of the disclosure and equivalents thereof.

Figure 1:
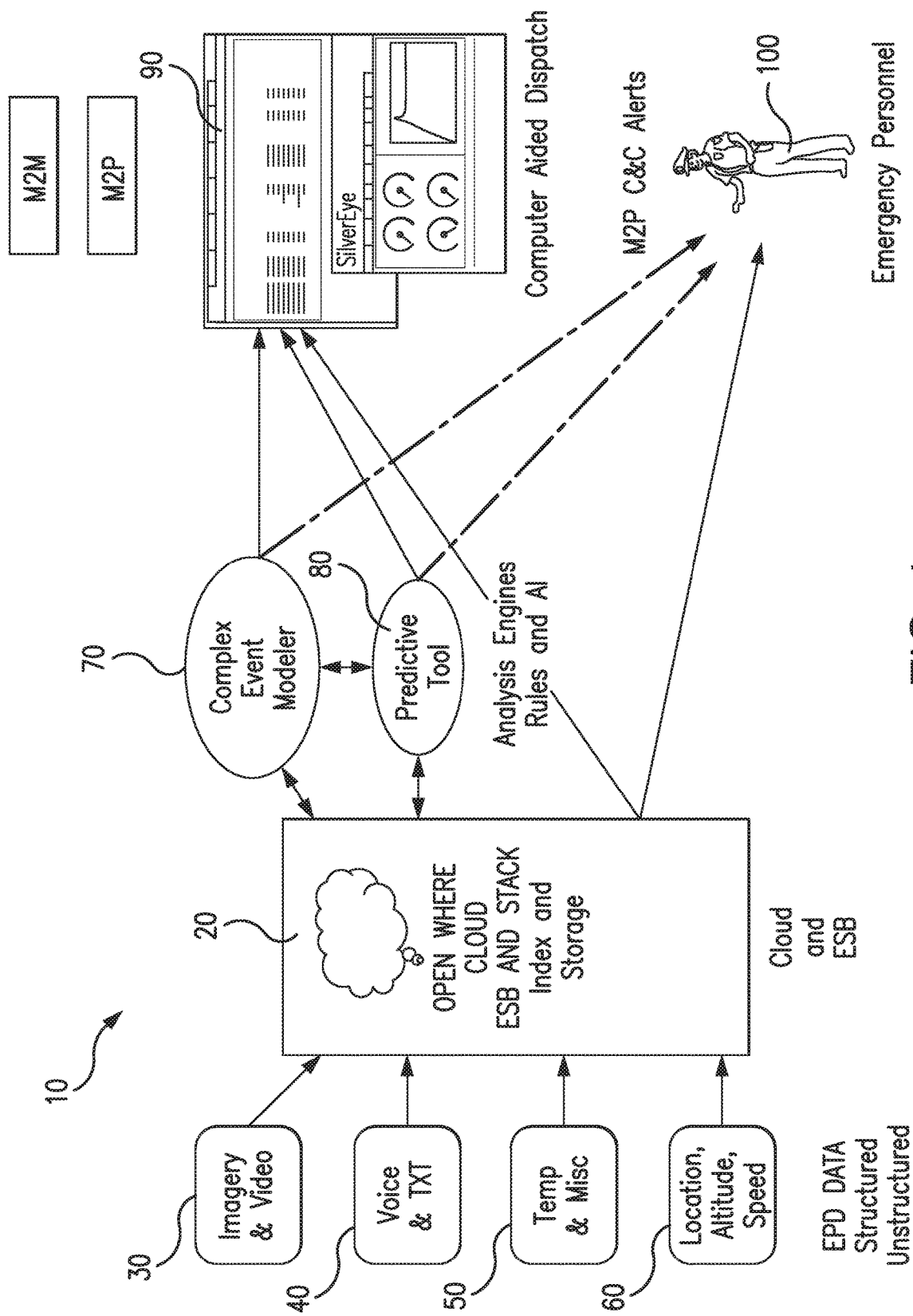
FIG. 1 is a diagram of the structure of a system according to an exemplary embodiment of the present invention.

FIG. 1 shows an exemplary embodiment of a system 10 in accordance with the present invention. Server 20 receives data from a plurality of user devices such as image and video data from device 30, voice and text data from device 40, temperature and other data from device 50, and location, altitude, and speed data from device 60. Thus device 30 includes a sensor such as a microphone and a camera, device 40 includes a sensor such as a microphone and a keyboard for receiving text data that may be embodied by a touchscreen displaying the keyboard, device 50 includes a sensor such as a thermometer, and device 60 includes a device such as a global positioning system (GPS) sensor. Devices 30, 40, 50, and 60 may be smartphones, tablets, digital cameras, laptop or desktop computers or any other electronic device capable of collecting and transmitting this data. Further, any of the user devices 30, 40, 50, and 60 may include more than one sensor, or all of the sensors listed above. In general, each of devices 30, 40, 50, and 60 will include at least one sensor, a processor, memory, a transmitter for transmitting the data to server 20, and a receiver for receiving data from server 20. Server 20 also includes a processor, a memory, a transmitter for transmitting data to devices 30, 40, 50, and 60, and a receiver for receiving data from devices 30, 40, 50, and 60. Devices 30, 40, 50, and 60 will be referred to hereinafter as end point devices (EPDs).

In one embodiment, the EPDs are portable electronic devices that run one of the Android®, iOS®, or Blackberry® operating systems. An app run by the device performs the functions described herein as performed by the EPD. An exemplary portable electronic device is a wearable electronic device including a video camera and microphone described in U.S. patent application Ser. No. 13/212,686. This application is incorporated by reference herein. IN another embodiment, the EPD may be a wearable (body worn) health tracking device such as the FitBit®, Pebble®, Basis Peak®, etc.

Server 20 may include a complex event modeler 70 and a predictive modeling tool 80 which analyzes the data received from the devices to determine if the data received from the devices corresponds to an event such as an emergency. The event can be a crime in progress, a severe weather event, or any emergency scenario where life or human/property security (e.g., child abduction, car break-in, arson, tornado, flash mob, etc.) is already or about to be imperiled. Server 20 manages and transforms event files and automatically generates notifications, including machine to machine (M2M) notifications, using a computer aided dispatch (CAD) tool 90, analytic tools, or command and control tools; and/or machine to person (M2P) notifications to a private or public actor 100 to respond to the event by sending an alert(s) to the actor 100 with information about the event derived from the uploaded data. The private or public actor can be an emergency first responder (law enforcement, fire, and/or ambulance), a crime investigation organization such as the FBI, public safety personnel, or a private security firm (such as hired for security at a sporting game like the Olympics, Super Bowl, or World Cup). The action taken by the actor can include dispatching one or more first responder(s), such as a fire truck, an ambulance, or a police vehicle and associated first responder personnel, or causing an amber alert to be issued, for example.

Complex event modeler 70 is the analytic engine inside the server 20 that allows thousands to millions of data feeds to come in from the EPDs and then alert on pre-defined thresholds. For example, if a fire is seen in a video the complex event modeler 70 will send an alert to the nearest fire department and send notices to EPD users in the immediate area. In one embodiment, complex event modeler 70 may include the GeoVigilance tool commercially available from Transvoyant.

Predictive modeling tool 80 is the analytic engine inside the server 20 that takes the alerts and data from the complex event modeler 70 and then "predicts" the next likely group of scenarios. For example, a fire on or near a major thoroughfare would generate an alert that indicates traffic will cause delays in the area and EPD users should plan accordingly. In one embodiment, predictive modeling tool 80 may include the SilverEye tool commercially available from Knowmadics, the Total Insight tool commercially available from Larus, or the Satellite Tool Kit (STK) commercially available from Analytical Graphics, Inc.

In one embodiment, CAD tool 90 includes the SilverEye web-based software application commercially available from Knowmadics, Inc. running in a CAD center. SilverEye may be the device management software in the system 10 that all the EPDs running the app are connected to. SilverEye in a CAD center allows data from EPDs to be visualized securely and quickly without having to replace the current investment legacy hardware/software in the CAD center. For example, a computer in the CAD center that has internet connectivity can visualize/playback imagery, video, and audio data from EPDs running the app as the data is collected to supplement the traditional data collected from a 911 call—location, voice description, and identity (phone number).

Alerts may be generated by the server 20 or CAD tool 90 based on the data received from the EPDs. For example, using SilverEye an operator can set an alert(s) based on certain conditions/groups of conditions being met or exceeded—location, time, key words, weather, and/or temperature etc. When the conditions set by the operator are met, the CAD tool 90 automatically generates an alert—machine-to-machine (M2M) or changes a condition on another device. For example, a geographic boundary/geofence can be created and when say 10 or more objects enter the boundary after 6 PM. Alerts may be generated by the server 20 or based on the data received from the EPDs. What triggers an alert—using SilverEye an operator can set an alert(s) based on certain conditions/groups of conditions being met or exceeded—location, time, key words, weather, temperature etc. that when the conditions are met automatically generates an alert—machine-to-machine (M2M) or changes a condition on another device. For example, a geographic boundary/geo-fence can be created and when say 10 or more objects enter the boundary after 6 PM, an alert can automatically be generated to a security guard to go check out the area for suspicious activity. In this case, an alert can automatically be generated by CAD tool 90 and transmitted to a security guard 100 to go check out the area for suspicious activity.

In another embodiment, server 20 or CAD tool 90 may generate alerts to be sent to EPDs by linking multiple EPDs to other types of devices such as cameras, audio recorders, trackers, seismic sensors, etc. For example, a geographic boundary can be set on the SilverEye control software so that when an EPD connected to system 10 enters, leaves, passes-by, etc. the geographic boundary an alert is generated which will enable a third party camera to track the EPD remotely without any human in the loop. That camera data can then be sent automatically to another EPD connected to system 10.

Figure 2:
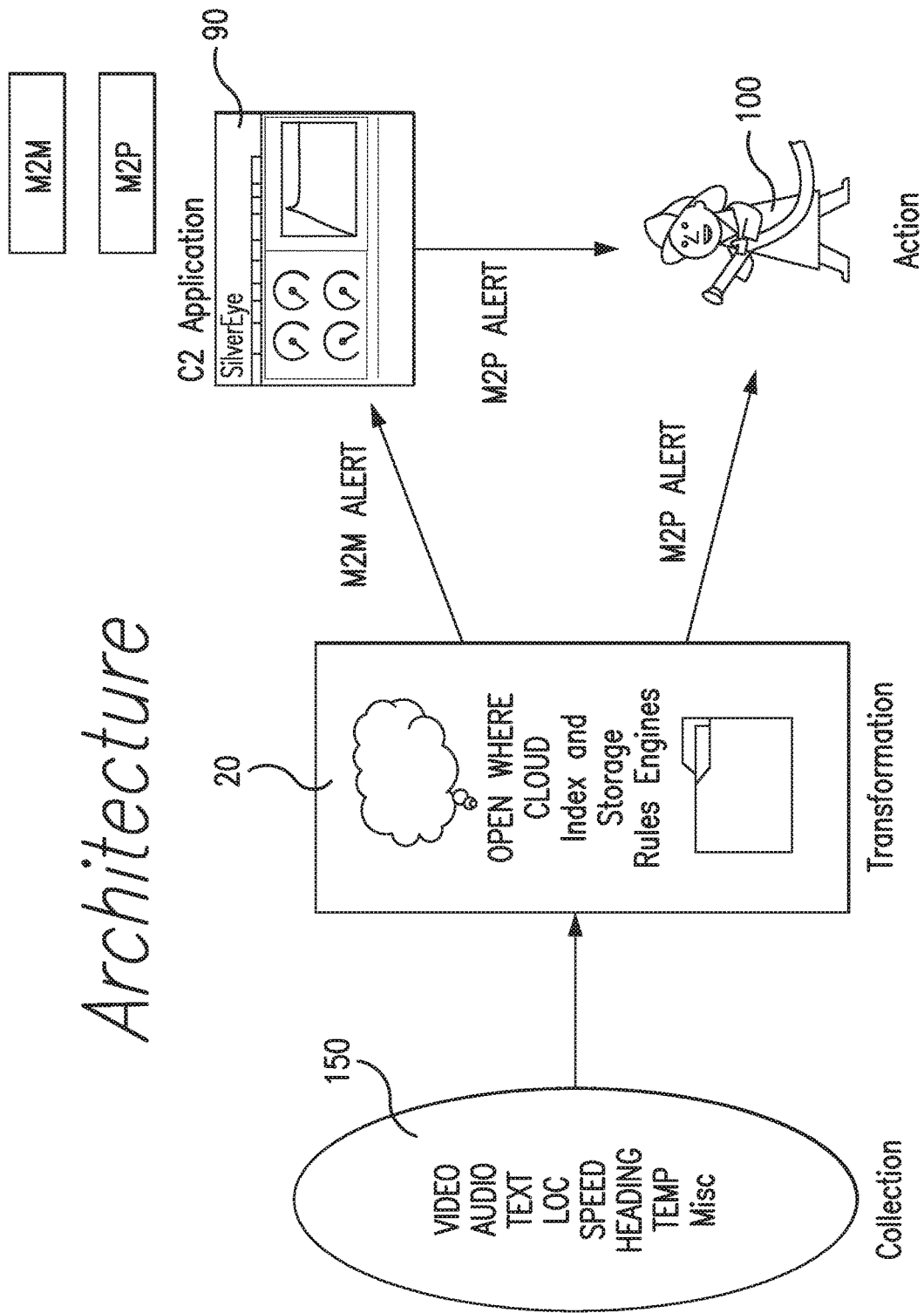
FIG. 2 is another exemplary system of the present invention.

In an exemplary embodiment shown in FIG. 2, EPD 150 is a smartphone capable of collecting all of the above described data, which runs an app to perform these functions. The app allows selectable wireless transmission of a known and/or anonymous user's geographic location coordinates, audio, video, voice, text, temperature, velocity, or altitude (or any other sensed data available on the EPD 150) to server 20.

Figure 3:
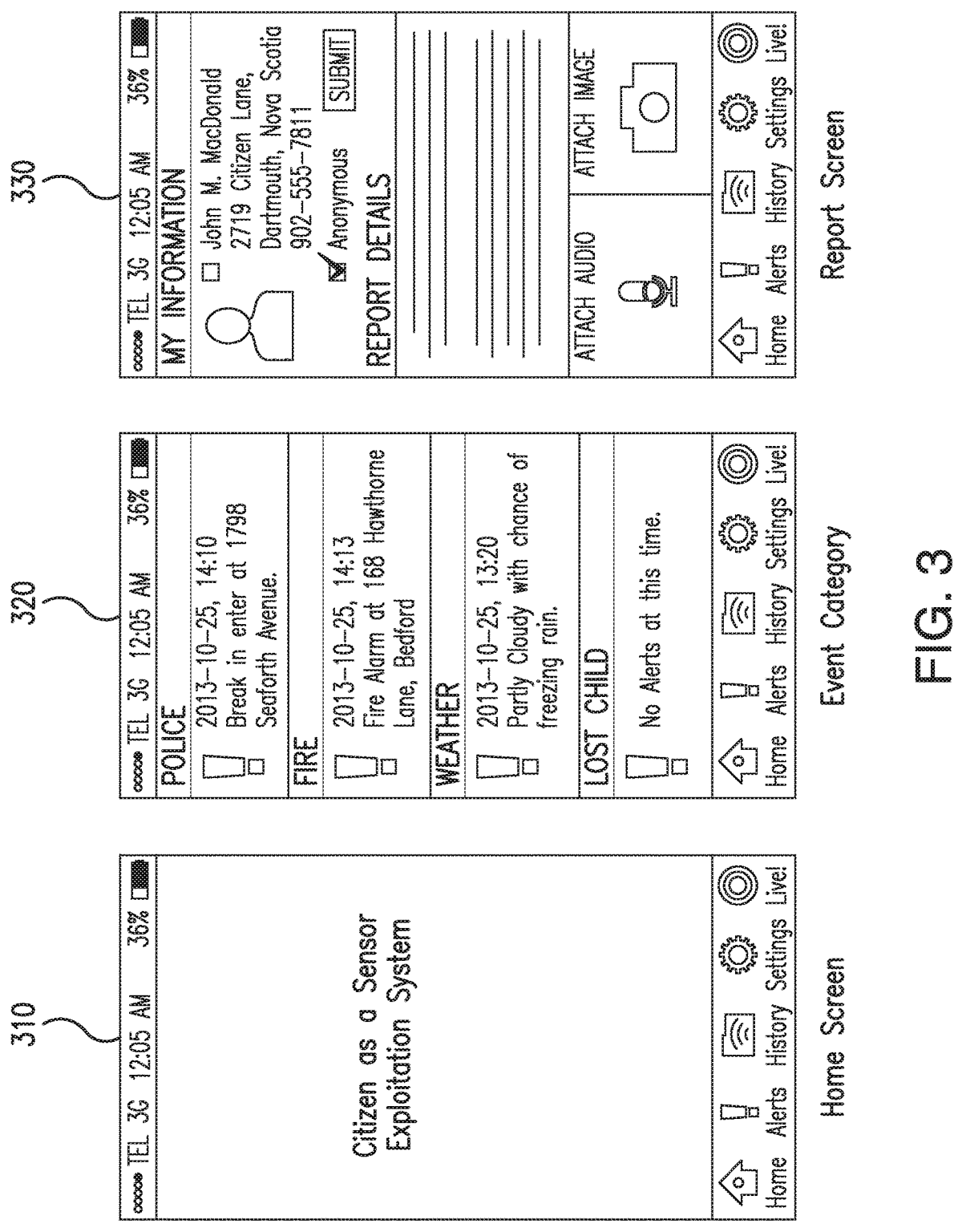

A user who witnesses an event can create a report on EPD 150 to upload to the server 20. FIG. 3 shows exemplary screen shots of EPD 150 creating a report. Screen 310 shows an opening menu for creating a report. Screen 320 allows a user to select a type of report (police, fire, weather, lost child, etc.). Screen 330 allows the user to remain anonymous, and add whatever type of data they have collected to the report. The report can include a text summary of the incident the user wishes to report, and audio/video/photo attachments. The user identifies the type of alert, and the report, attachments are uploaded to the remote system, with the option to retain a copy of the report or to transmit without storing any data on the user's EPD. Multiple users (the crowd) witnessing the same incident/event can upload reports and sensor data about the event to the same remote system in a crowd-sourcing model. Data previously collected on the EPD 150 by other existing apps can be added to a CASES/AGENT report. For example, an image that was taken on an iPhone with the iOS® Camera app can be appended to a CASES report which is sent to a CAD tool 90.

Figure 4:
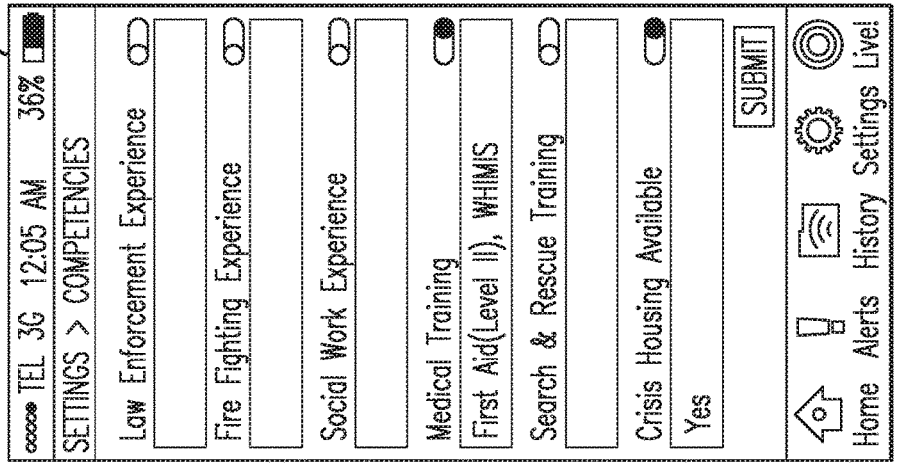
Figure 4:
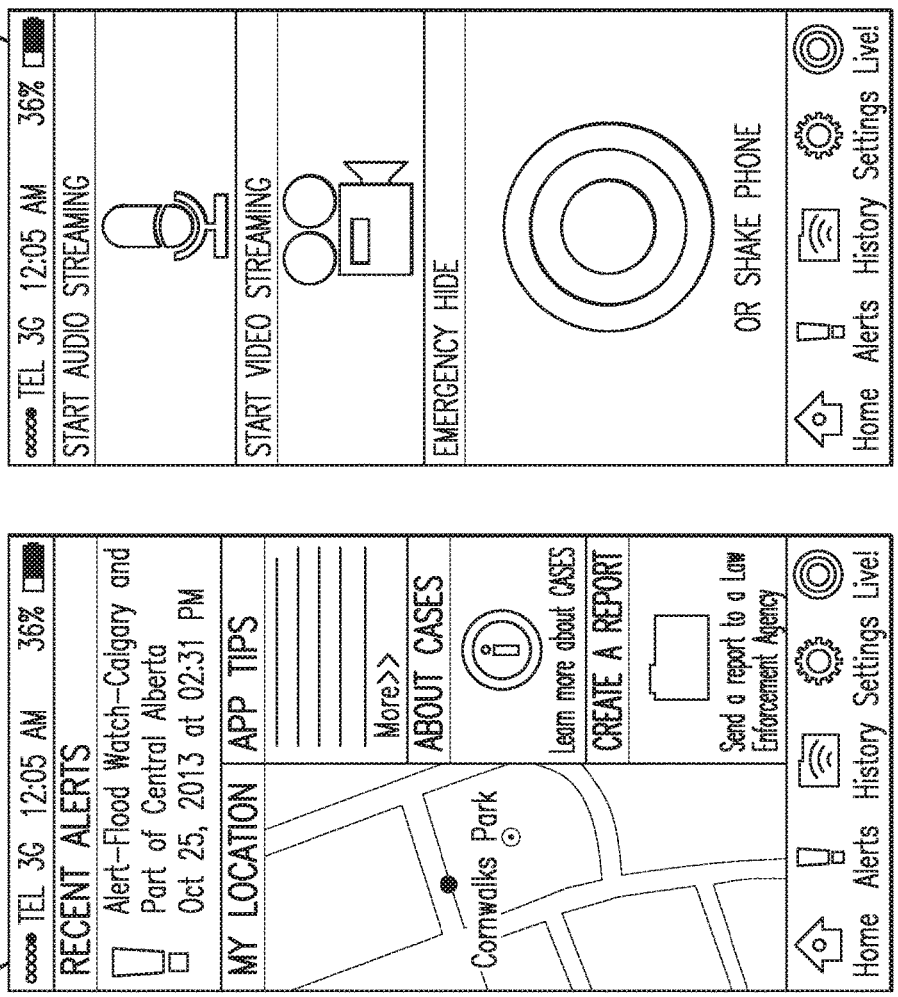

As shown in FIG. 4, screen 410 shows alerts that other users in the vicinity of the event, and who have authorized their EPDs to receive alerts, can receive from the remote system 20 about the ongoing event. Screen 420 allows the notified user to provide further data to server 20. Screen 430 allows the user to notify the server 20 of the user's own skillset or competency (e.g., law enforcement, firefighting, social work, medical training, search and rescue, crisis housing), and if the event calls for a particular competency, the remote system can automatically send alerts to all users with competencies relevant to the event and who are located in the vicinity of the event information about the event so that the user can utilize their competencies to ameliorate negative consequences caused by the event. Such users would have authorized the app to track their location so that the remote system can send alerts only to those users located close to the event of interest, regardless of whether those users have witnessed the event or submitted a report.

Figure 5:
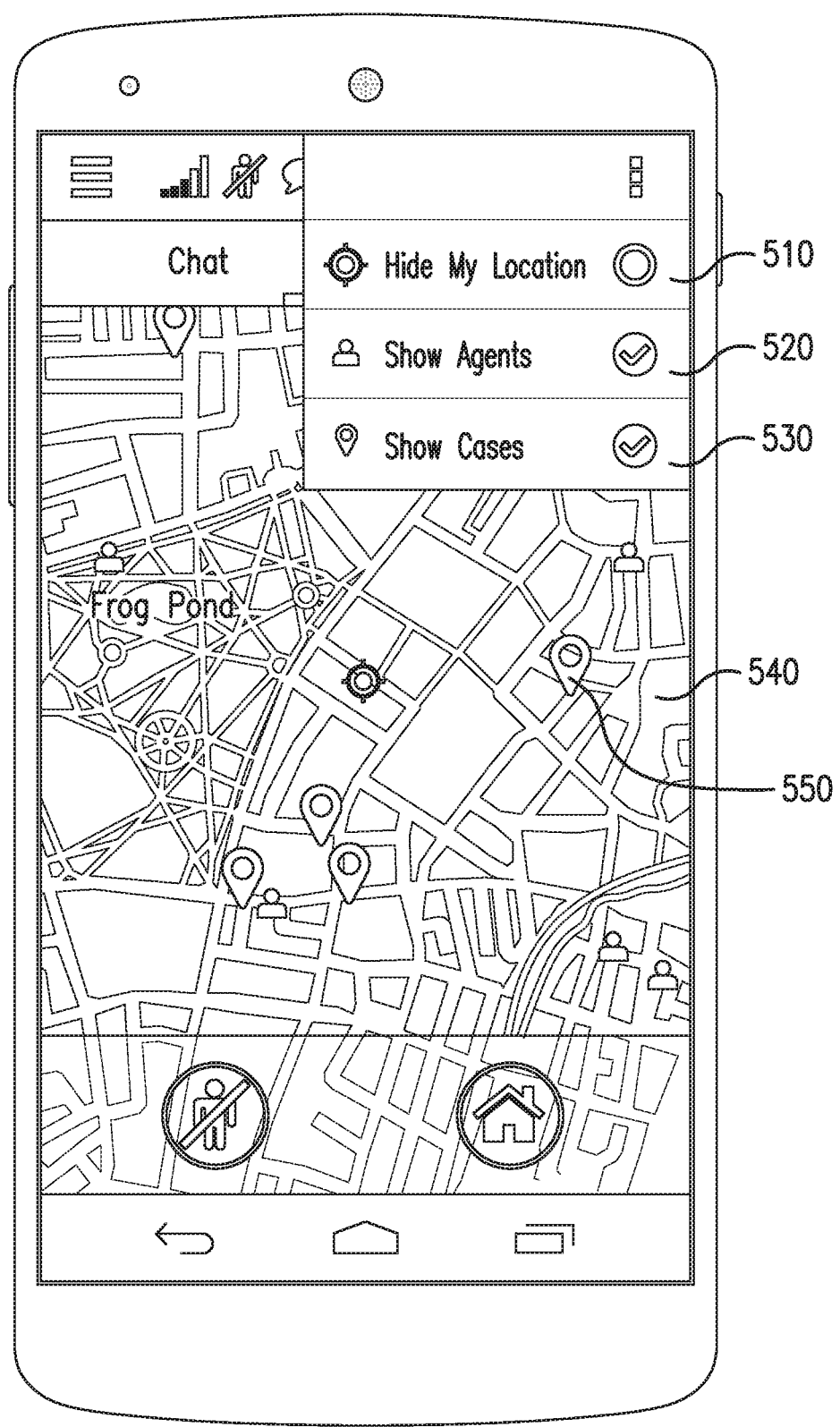
FIG. 5 illustrates a screen shot of an embodiment of the present invention where the client can display reported cases to a user on a map.

The server 20 can also provide a list of previously submitted reports to the EPD 150. As shown in FIG. 5, the EPD can display a map 540 with indicators 550 at each report location. Menu buttons 510-530 allow the user to select whether the map will include indicators to show their own location, other agents, and/or the report locations ("cases"). In the embodiment shown in FIG. 5, the user's own location is being shown, with the map roughly centered on the user's location. Even if the user's location is turned off with button 510, the map may still be centered on the user's location as a default state. The map shown in FIG. 5 is a street map, but any local map is within the scope of the invention, such as maps of stadiums as discussed below.

Figure 6:
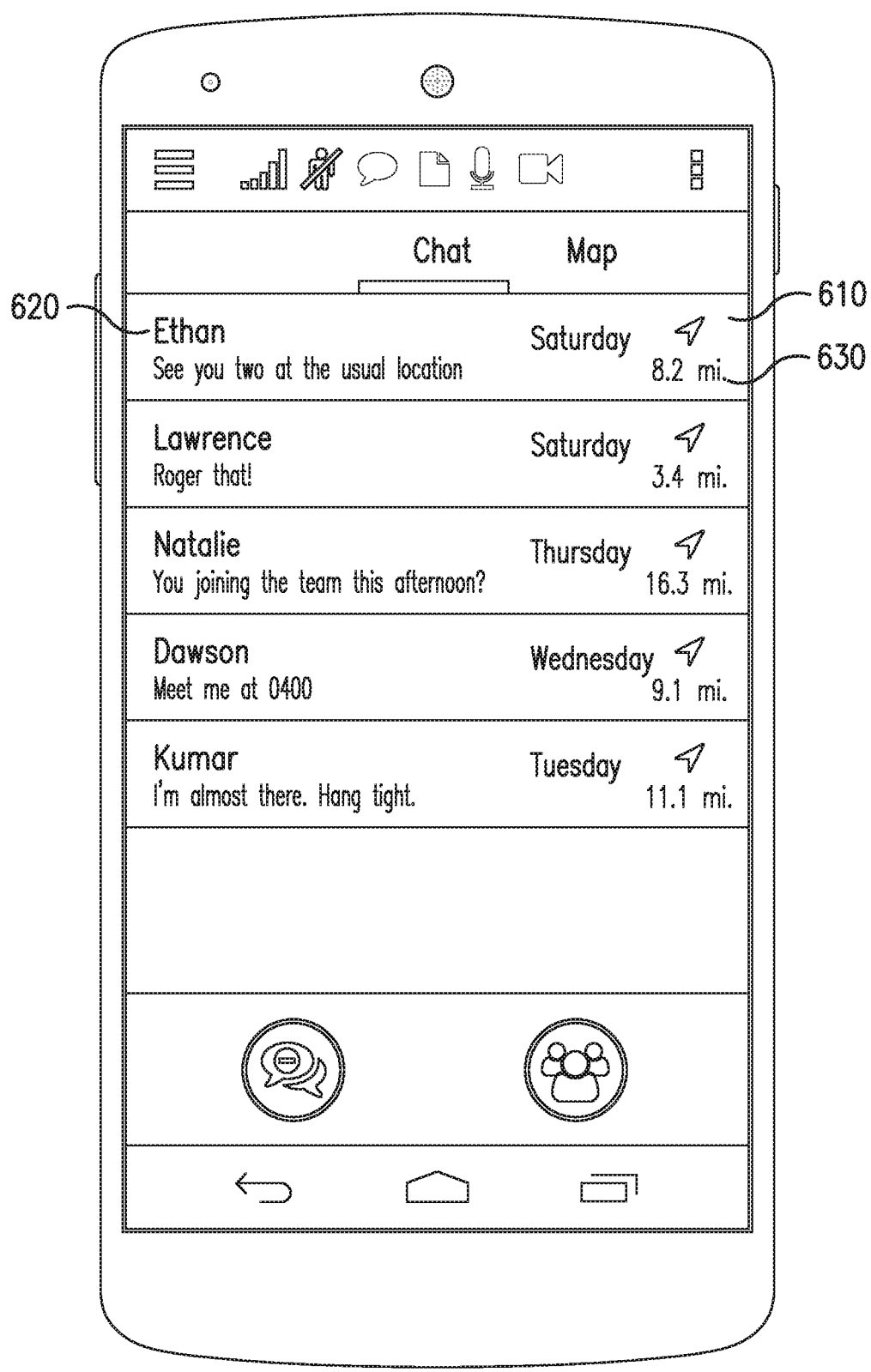
FIG. 6 illustrates a screen shot of an embodiment of the present invention where the client can display locations of chat participants.

Further, the EPD can support a chat function which allows the EPD user to chat as shown in FIG. 6. The EPD can display the distance 630 and direction 610 of a plurality of chat participants 620 so that the user can directly gather further information about local events, or warn others.

Figure 7:
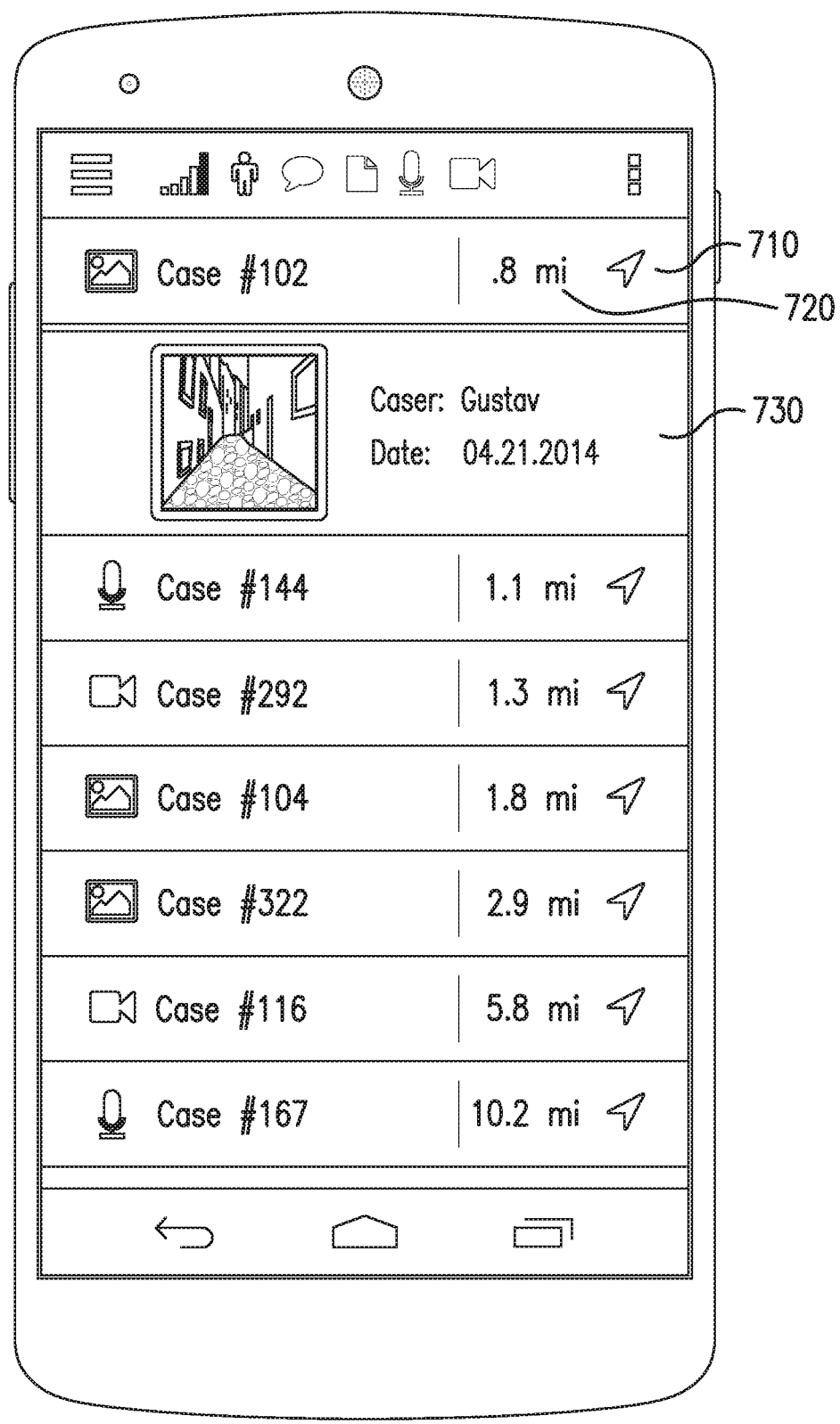
FIG. 7 illustrates a screen shot of an embodiment of the present invention where the client can display a list of reported cases and provide additional information on a selected case.
Figure 8:
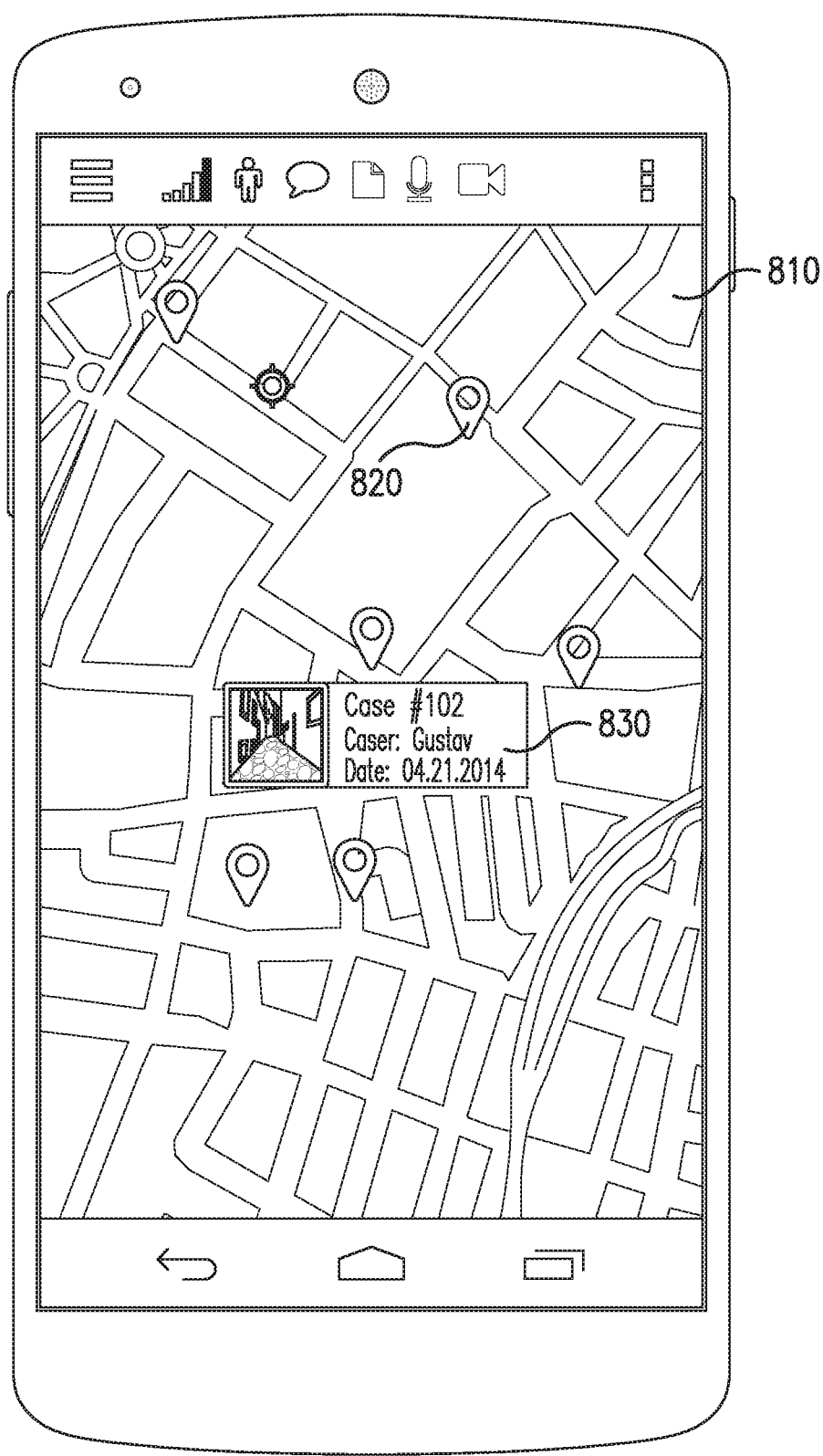
FIG. 8 illustrates a screen shot of an embodiment of the present invention where the client can display reported cases to a user on a map with additional information for a selected case.

FIG. 7 shows that the EPD displaying a list of local cases, along with the direction 710 and distance 720 to the location of the case. When a user selects a particular case, further information 730 is provided. This further information may include some or all of the data the reporting EPD provided to the server 20. This further information may be displayed on the map proximate the location of the case, as shown in FIG. 8. FIG. 8 illustrates an exemplary map 810 with case location markers 820 and case information 830.

Figure 9:
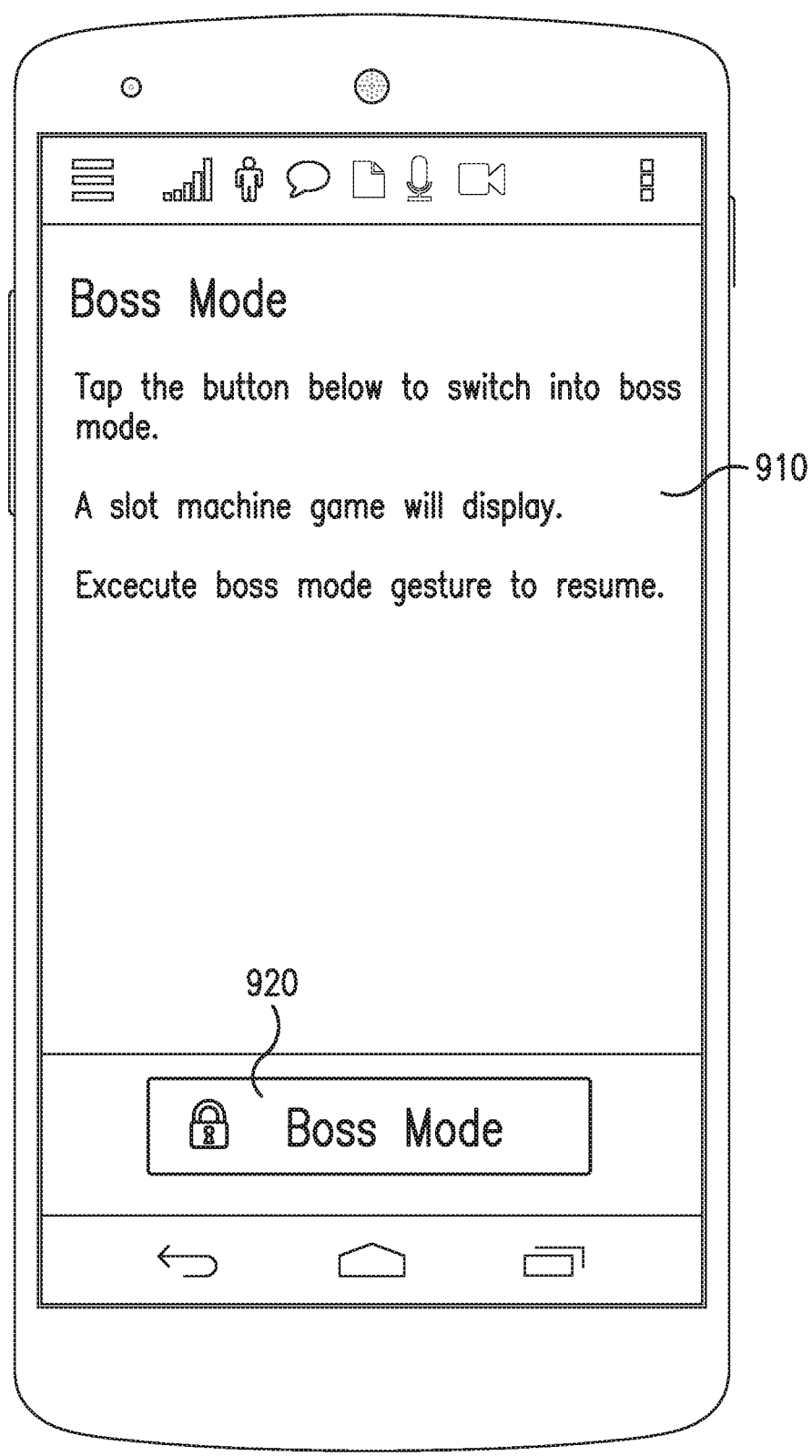
FIG. 9 illustrates a screen shot of an embodiment of the present invention where the client can be manually set in a boss mode.

Any user can also authorize the EPD to turn any selected sensor on the EPD on or off (e.g., microphone, camera, GPS, accelerometer) and upload the selected sensor outputs in real time to the server 20. Further, by selecting the boss mode button 920 shown on screen 910 of FIG. 9, this can be done surreptitiously for the safety of the user. In this case, an innocuous screen is displayed during data collection, such as the exemplary game display 1000 shown in FIG. 10. Any screen unrelated to data collection may be used to prevent a hostile person from seeing that the user is collecting and reporting data, possibly related to a crime being committed by the hostile person.

In another embodiment, server 20 issues a command to the EPD 150 to enter boss mode without any command by the user of EPD 150. In this regard, a rule set can be established by server 20 based on conditions being met that would automatically enable collection to occur on the EPD 150 without the user having to do anything. In one embodiment, server 20 can command each EPD 150 to start recording/streaming video whenever the EPD 150 was within 1 mile of a landmark such as the Washington Monument. In another embodiment, the server 20 may command every EPD 150 within a set distance of a reported case to begin recording sensor data and to transmit the sensor data to server 20.

Figure 11:
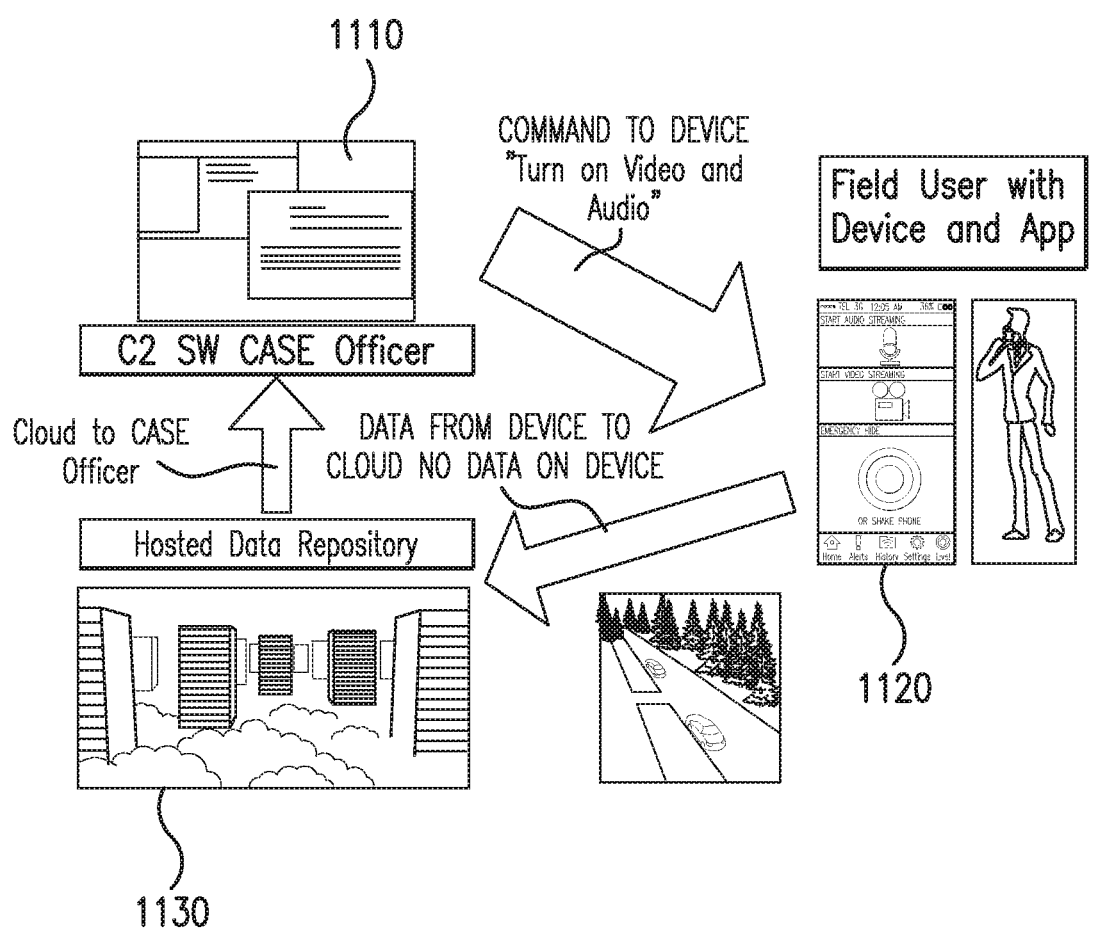
FIG. 11 illustrates another exemplary system according to the present invention.

The EPD also allows the user to select three levels of participation: anonymous in which the user uploads reports or sensor data anonymously, passive in which the user's personal identification information is reported with the sensor data uploaded, and remote control in which the user allows the remote system to control one or more sensors on the user's EPD for transmission to the remote system. The EPD can be placed in an invisible or surreptitious mode in which it will transmit sensor data in the background without conveying any human-discernible cues that it is doing so. In this regard, FIG. 11 shows that a server 1110 can send a command to device 1120 to collect and transmit data without the user knowing. The data is sent to repository 1130 to be analyzed by server 1110.

Figure 12:
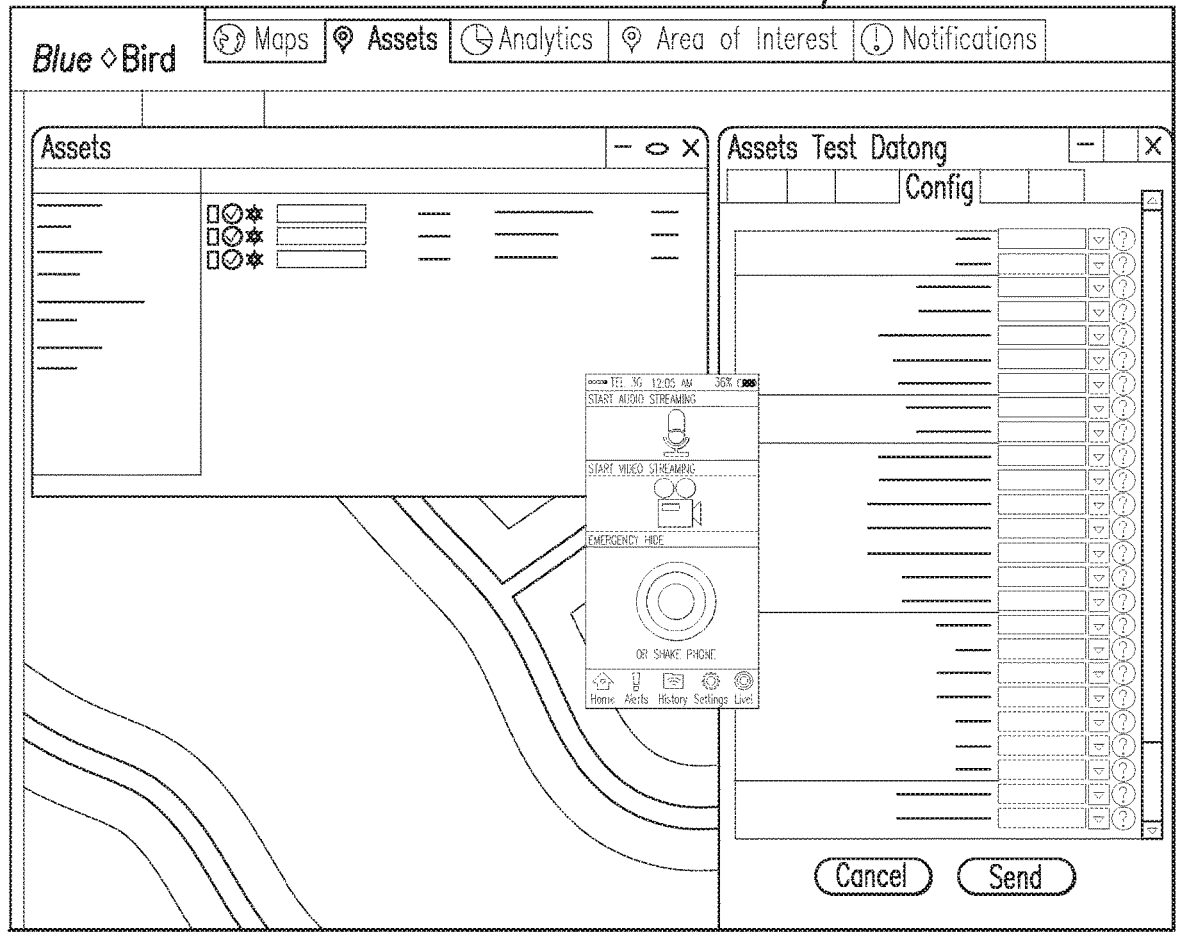
FIG. 12 illustrates an exemplary server that may be part of the systems shown in FIGS. 1, 2, and 11.

FIG. 12 shows an exemplary display of the CAD tool 90, which may be embodied by SilverEye™ software. The features of this tool are described above with respect to FIG. 1.

In another exemplary embodiment, the above described features may be divided between two apps, the CASES app and the CASES AGENT app. CASES and CASES AGENT apps are distributed on EPDs with back end support provided through a cloud model controlled via an enterprise service bus (ESB). The primary CASES app turns EPDs into sensors and those sensors can be used in a crowd-sourced fashion to help law enforcement, public safety, and defense personnel in a time of crisis or danger. The CASES ecosystem involves the software app and the software back end data transformation which occurs in the cloud as data from the EPDs is analyzed and in the cloud. The CASES AGENT app has secondary features that allow it to be used (turned on and off) remotely.

Primary features include:

Philosophy of CASES and CASES AGENT=Collection-Transformation-Action

CASES and CASES AGENT are part of an ecosystem that includes a downloadable app which connects to a cloud based transformation engine which then sends machine to machine (M2M) and/or machine to person (M2P) alerts which cause action to occur in the real world.

It was designed primarily for everyday use as well as venue/event specific use. End users (civilians) can see an event and send data as quickly and easily as possible as an enhancement to public safety.

Data is received by the CASES back end processing capability in the cloud transforms the raw data feeds into a case.

The app can be customized by end users and white labeled for specific events—such as the Superbowl, Olympics, World Cup, Grand Prix, etc. In those instances the actual seating chart of the venue could be downloaded as an add on and users in the ecosystem can identify where they are sitting/standing so that when an event occurs the data they generate can be tied to a specific area within the event.

Uses the off-the-shelf/out-of-the-box capability of the EPDs to send data—location, audio, video, text, temperature, speed, altitude and any other data that can be collected by the EPD to the cloud for follow on analysis, cataloguing, and distribution.

Quick way for average citizen to share observations from their EPDs.

Venue Specific downloads are available so that at an event CASES users can let people know where they were sitting/standing etc. when an event occurred.

Everyday CASES users can register any particular skill set they have that would make them more useful in an actual emergency so that officials would know what type of Good Samaritan support there was near an emergency.

CASES reports can be shared with public safety and law enforcement personnel.

Directly to Law Enforcement, public safety, or to a "Cut out" server which is accessible by personnel at a computer aided dispatch (CAD) center or public-safety answering point (PSAP), sometimes called "public-safety access point" (a call center responsible for answering calls to an emergency telephone number for police, firefighting, and ambulance services). This CAD center may house the CAD tool 90 as described above.

An enhanced version of CASES called CASES AGENT has all of the same capability plus listed above plus:

The AGENT version can be remotely controlled by command and control (C2) software in server 20 to turn on/off the camera, audio and locational data streams from EPD 150 the AGENT version is hosted on, as shown in FIG. 11. This command to enter boss mode by the server 20 does not involve any input by the user of EPD 150, as discussed above.

AGENT Version has a panic button feature.

Figure 10:
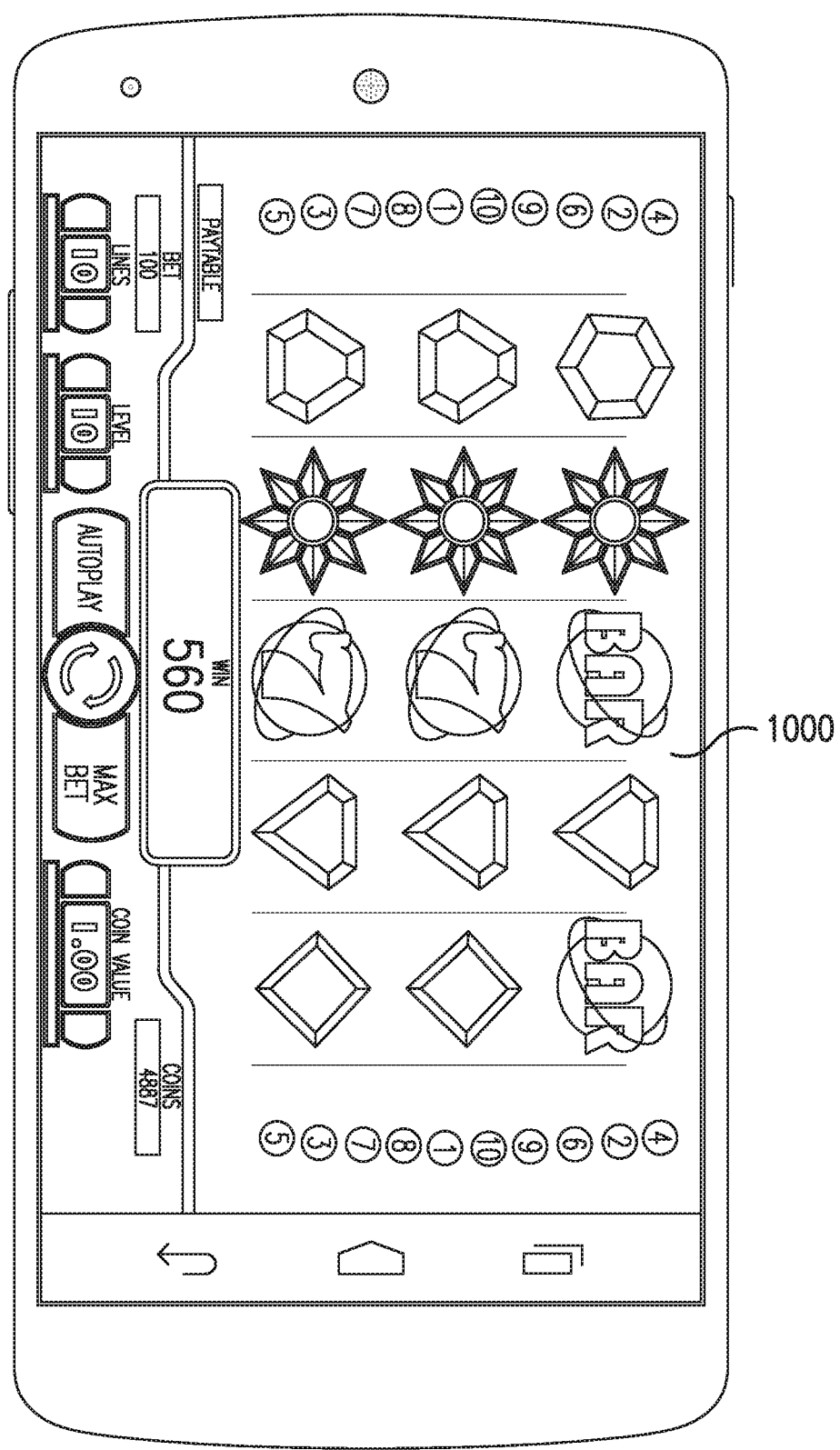
FIG. 10 illustrates a screen shot of an embodiment of the present invention where the client is currently in boss mode.

AGENT Version has a manually selected boss mode so that a user can make it appear as if the app is not running if they had to turn their EPD over for forensic inspection, as shown in FIG. 10.

AGENT Version has a primary mission of information collection for public safety.

AGENT Version can be scheduled to turn and off based on time of day and/or location.

The remote system can communicate with, for example, the FBI, the DEA, other law enforcement, public safety, or military operations.

Thus, the CASES and CASES AGENT app technologies combine crowd sourcing with civic responsibility to create an ecosystem where modern technology—specifically the billions of dollars of investment in EPDs and the cloud—can be used to do good. It puts technology that is already in the hands of ordinary citizens to work for the common good. Some advantages of the CASES and CASES AGENT app include that it creates a central application to process and fuse multiple types of data from EPDs and then easily send it from the EPD to the cloud with a simple buttons.

The CASES and CASES AGENT apps are designed to be customized so that it can be licensed to a sponsor who becomes the sponsor of the app being used at specific events such as the Olympics, etc. It can be customized so that certain EPD features can be turned on and turned off in countries where data collection of this type is prohibited.

Additional advantages of the invention may include (this list is not exhaustive):

1. Single screen app interface—as opposed to 2-4 separate applications with multiple interfaces, such as having a separate app to track a phone, an app to take a picture, an app to record audio, an app to record a video, or an app to chat.
2. Multiple date feeds from multiple EPD sensors—as opposed to a user experience where each screen can only handle one feed at a time.
3. Crowd sourced data inputs from social media—as opposed to just getting one way notification alerts from a Rich Site Summary (RSS) feed or broadcast.
4. Can be used as an information collection and transmission tool in real time—as opposed to collecting data and then sending it at a later date in response to an alert or after an event. For example, the Boston Marathon Bombing had thousands of people collecting images and video, but without any way to easily and rapidly transmit that data to public safety and law enforcement personnel. The FBI was forced to manually collect data from EPDs from witnesses and then fly that data from Boston, Mass. to FBI facilities in Quantico, Va.
5. Open Application Programming Interface (API) and Software Development Kit (SDK) so that end customers can enhance and extend the software themselves—as opposed to a closed, proprietary system, or non-existent SDK or API that forces end users to pay the developing company to extend the capability.
6. Secure data transmission using Triple Data Encryption Standard (DES) or Advanced Encryption Standard (AES) 128/256 encryption for communications between the EPDs 150 and the data server 20.
7. Multi-modal data transmission pathways from the EPD 150 where data can be transmitted from the EPD 150 through either commercial terrestrial telephony (2G, 3G, 4G, LTE, etc.), WiFi, and/or satellite communications pathways.

Applications for the aspects of the present disclosure include:
1. Public safety
2. Emergency response
3. Crime prevention
4. Law Enforcement
5. Intelligence collection
6. Military/law enforcement hostile forces tracking
7. Military/law enforcement blue force (Agent/CI) tracking
8. Military/law enforcement mission planning
9. Military sensor planning
10. Critical installation protection Multiple applications can be used in parallel and then combined on the server 20.

Another exemplary embodiment of the present invention is the SNEEZES application, shown in FIGS. 13-16. SNEEZES is an acronym for Syndromic Notifications for Epidemics or Elevated Zone Events System. The SNEEZES app technology combines crowd sourcing with civic responsibility to create an ecosystem where modern technology—specifically the billions of dollars of investment in EPDs and the cloud—can be used to do good. It puts technology that is already in the hands of ordinary citizens to work for the common good. Advantages of the SNEEZES app include that it creates one central application to process and fuse multiple types of data from EPD and then easily send it from the EPD to the cloud with a simple buttons.

Figure 13:
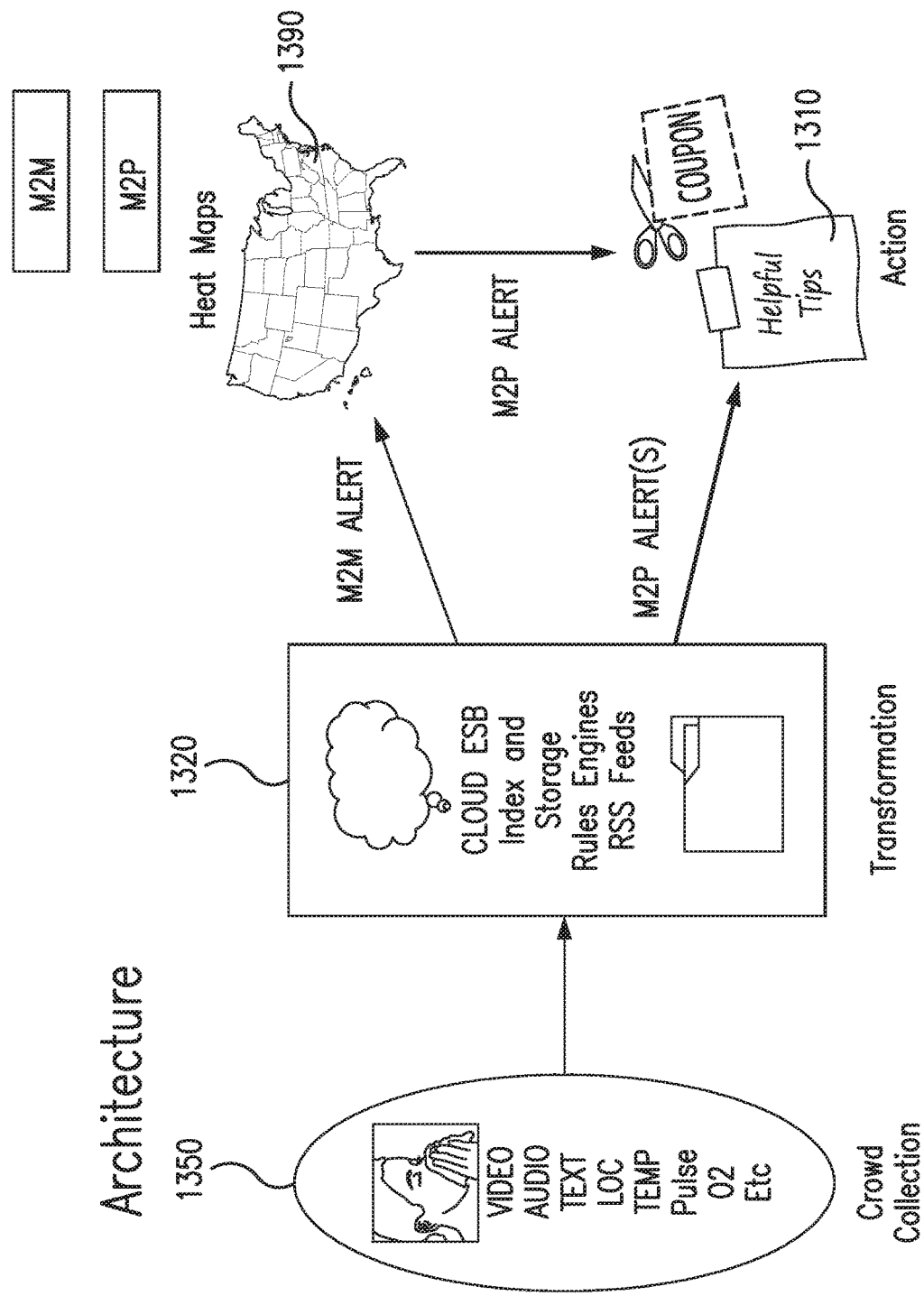
FIG. 13 shows a system according to another exemplary embodiment of the invention.

In this regard, FIG. 13 shows an exemplary SNEEZES embodiment including EPD 1350 collecting and transmitting data as described with respect to the previous embodiments. The SNEEZES system thus includes a data collection, transformation and action ecosystem that includes a) an app front end for data collection where the data is provided by end users voluntarily about their general health from EPD 1350, b) a hosted cloud-based enterprise service bus (ESB) for data transformation 1320, and c) a hosted web site for the publication of "heat maps" 1390 made from the transformed data from app users. The heat maps 1390 can be viewed and distributed to on desk top as well portable platforms (laptops, phones, and tablets). A heat map 1390 is a graphical representation of data where the individual values contained in a matrix are represented as colors. In one embodiment of SNEEZES, the heat maps 1390 represent instances of people reporting feeling unwell or well.

EPD 1350 includes a sensor such as a microphone, a camera, a keyboard for receiving text data that may be embodied by a touchscreen displaying the keyboard, a thermometer, and a global positioning system (GPS) sensor. Further, EPD 150 may include more than one sensor, or all of the sensors listed above. In general, each EPD 150 will include at least one sensor, a processor, memory, a transmitter for transmitting the data to ESB 1320, and a receiver for receiving data from ESB 1320. ESB 1320 also includes a processor, a memory, a transmitter for transmitting data to the EPD 1350, and a receiver for receiving data from EPD 1350.

People like to talk about their health. The primary SNEEZES app allows the public to report in near-real-time about their general health. That data is then collected in the cloud and transformed into heat maps 1390. Those heat maps 1390 can then have additional data sources overlaid on top of them to create dynamic and static views of population centers and the general health of people around them.

Further, alerts 1310 may be sent by the ESB 1320 to the EPD 1350. These alerts may include health information, location information, and may also include advertisements to pharmacies, drug store chains, event hosts, and/or tourist bureaus, based on how the user is feeling.

In another embodiment, an initial threshold can be set in a complex event modeling tool within ESB 1320 such that if more than 100 unique SNEEZES app users report flu symptoms within 50 miles of each other it will trigger the control system to do a web search of that area for reports of flu. If both conditions are met, ESB 1320 will send an alert to the EPD 1350 of all SNEEZES app users in the area to warn of increased possibility of the flu.

In still another embodiment, the SNEEZES app may have the ability to automatically transmit body temperature data off of EPDs 1350 which can record body temperature. If a person in a quarantine area uses a SNEEZES enabled EPD 1350, it would allow that persons' body temperature to be automatically recorded and forwarded through the SNEEZES app to a complex event modeling tool within ESB 1320 and aggregated with other SNEEZES collected data, as well as other third party collected data, to generate alerts back to EPDs 1350 of SNEEZES App users, as well as the general public.

Figure 14:
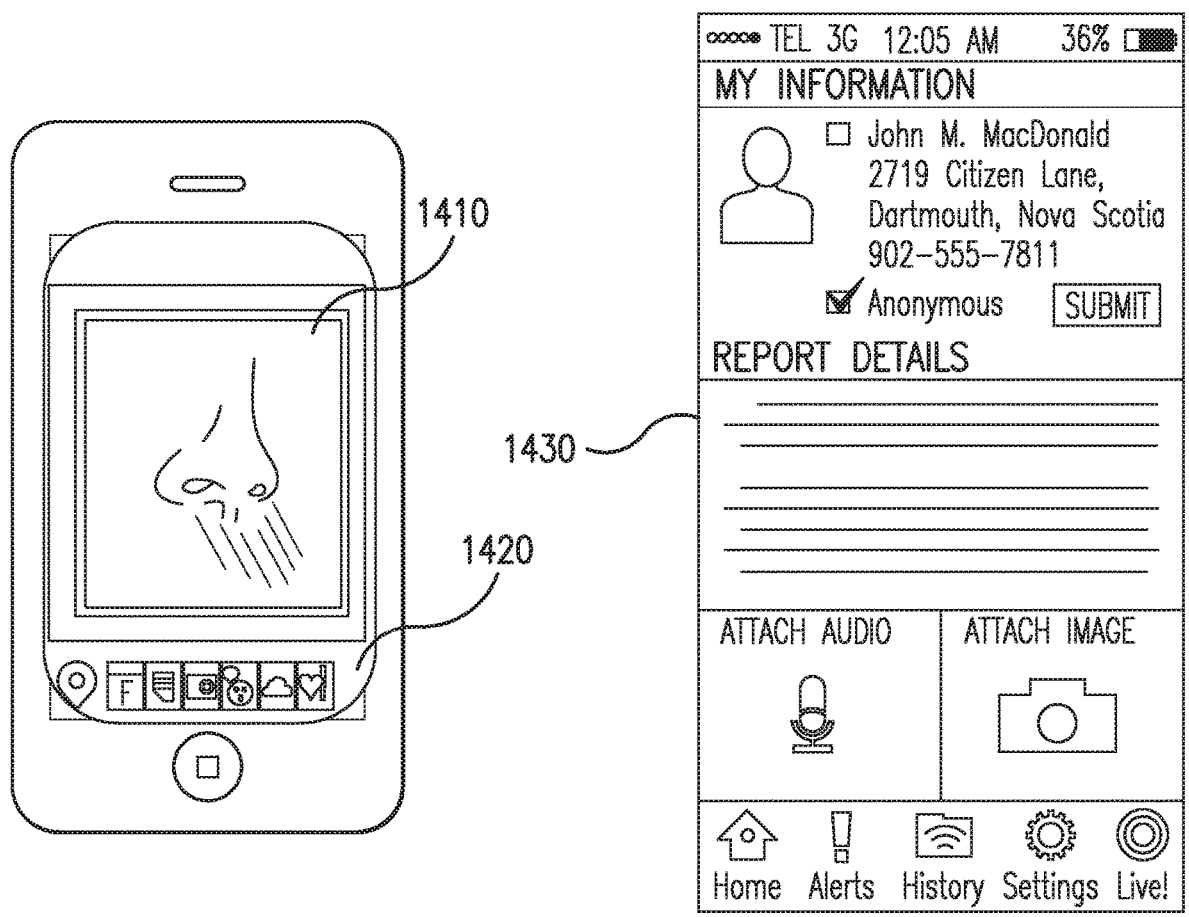
FIGS. 14-16 show exemplary screen shots of a client device that may be used with the embodiment shown in FIG. 13.

FIG. 14 shows a display 1410 and a menu 1420 to allow a user to report their health information. Screen 1430 shows that the user can remain anonymous, and may attach any of the data collected to their health report before sending to ESB 1320.

Figure 15:
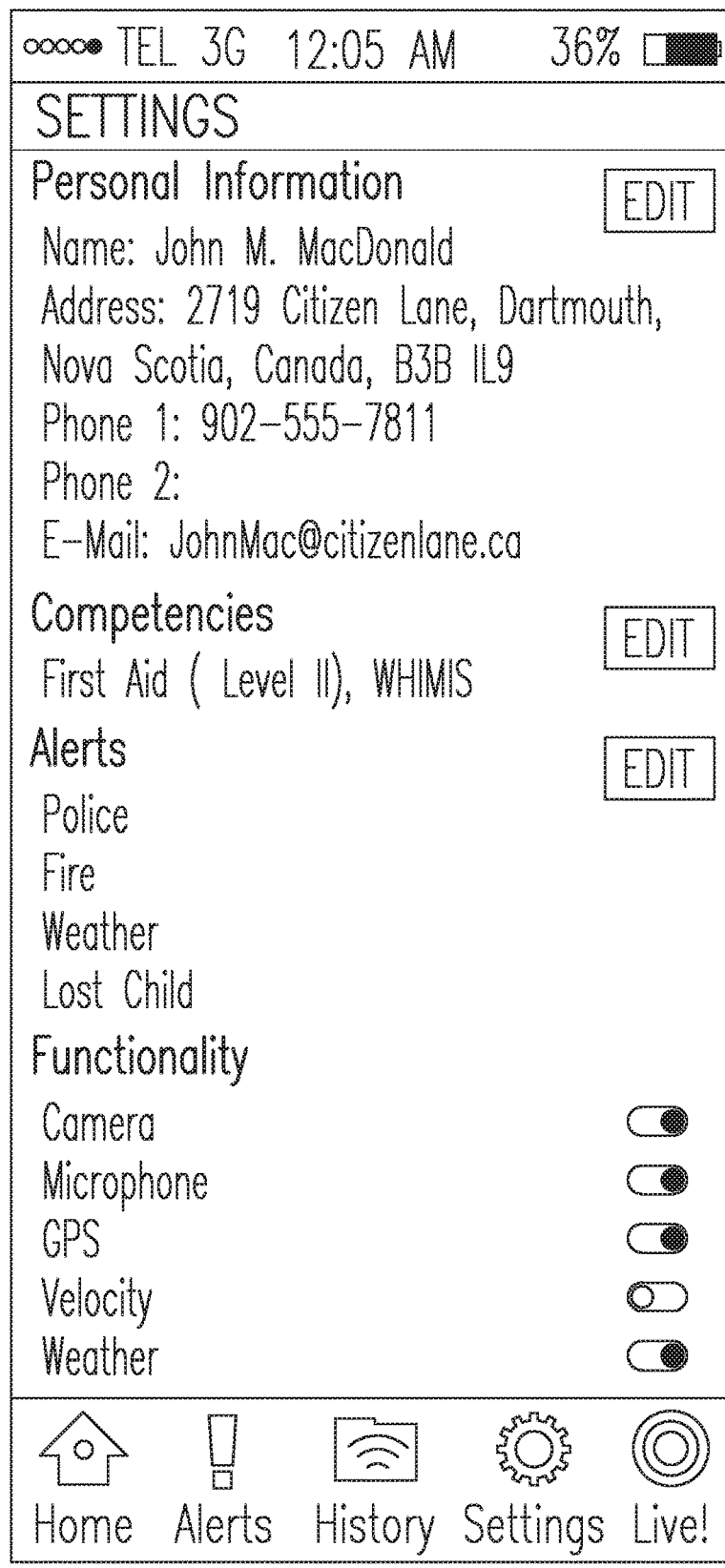

As shown in FIG. 15, the user can edit personal settings, which may include their own competencies that they can provide the ESB 1320.

Figure 16:
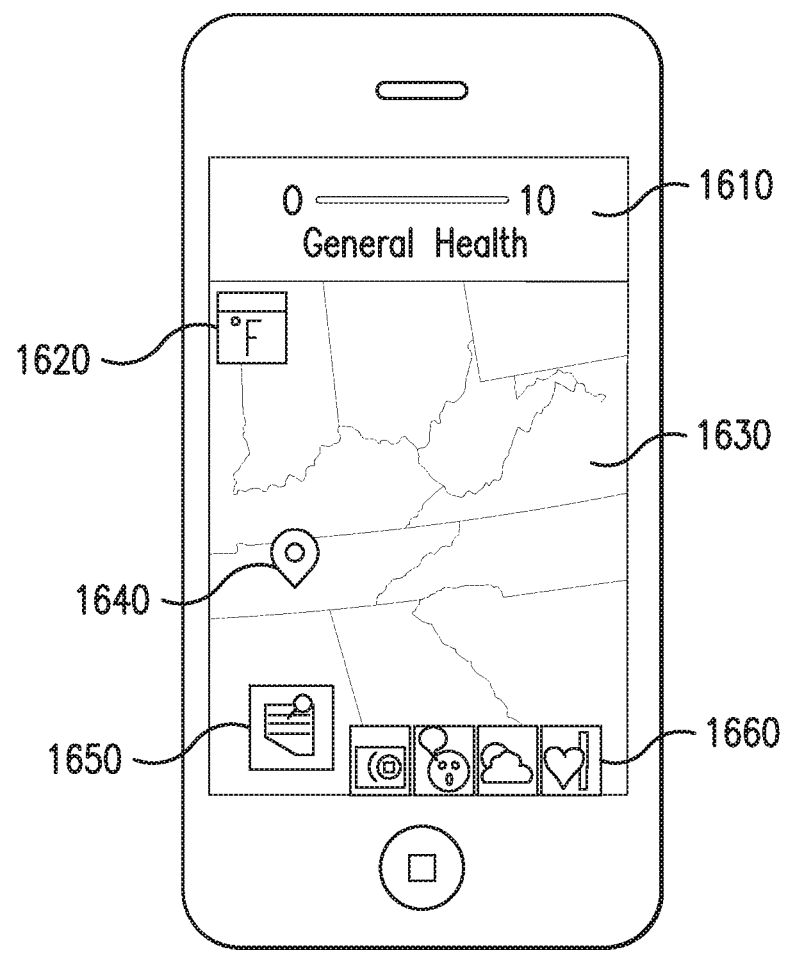

FIG. 16 shows one embodiment of a display of a heat map 1390. In FIG. 16, menu bar 1610 allows a user to designate a number from 1-10 to indicate their general health. Button 1620 allows the user to enter and post their body temperature. The heat map 1630 shows different colors based on health conditions in that locality. The user's location is at indicator 1640. The user can post text related to their health condition using button 1650, and the user can enter their heart rate using button 1660.

Thus in one embodiment, a user of the EPD 1350 enters data about their own health into EPD 1350 using the interface described above. The EPD 1350 sends the data entered by the user about their health to the ESB 1320. The ESB 1320 incorporates that data into heat map 1390 and transmits the updated heat map 1390 to EPD 1350, which can then display it for the user. Accordingly, the user can receive near-real-time updated heat maps providing health data covering the mapped area.

Philosophy of SNEEZES=Collection-Transformation-Action

SNEEZES is an ecosystem that includes a downloadable app which connects to a cloud based transformation engine which creates heat maps 1390 then sends machine to machine (M2M) and/or machine to person (M2P) alerts which cause action to occur in the real world.

It was designed primarily for "everyday use" for the public to contribute near-real-time experiential public health information to the larger public for multiple end user purposes, including:

Get help
Get coupons
Get travel information
Other

Data is received by the SNEEZES back end processing capability in the cloud transforms the raw data feeds into a SNEEZES heat map 1390 which then shows people their information in context and allows browsers of the data to see the general health and wellbeing of a population area prior to going there or for general situational awareness.

Additional RSS feed data for pollen count, heat index, health warnings, etc. would also be overlaid onto the SNEEZES heat maps 1390 to create a holistic public health snapshot informed by multiple sources including SNEEZES users. This enhanced level of syndromic situational awareness could prevent issues like asthma attacks in areas where heat, pollen, and other events may trigger an attack.

The app can be customized by end users and white labeled for specific events—Superbowl, Olympics, World Cup, Spring Break, Ski Season, Mardi Gras, etc.

People going on or hosting trips and/or to these venues could make use of the data as a way to show how healthy the area they are going to might be in relation to other parts of the country.

Uses the off-the-shelf/out-of-the-box capability of the EPD to send data—location, audio, video, text, temperature, heart rate, pulse $O_2$, etc. and any other data that can be collected by the EPD to the cloud for follow on analysis, cataloguing, transformation and/or to generate a heat map.

Quick way for average citizen to share observations from their EPDs about their general health and to see the general health of other parts of the globe.

Venue-Specific downloads are available so that at an event SNEEZES users can let people know where they were sitting/standing etc. when an event occurred SNEEZES reports can be shared with public safety and health officials either directly to them or to a "Cut out" server they have access to.

The apps are designed to be customized so that it can be licensed to say a corporation or tourist bureau so that they become the sponsor of the app being used at specific events such as the Olympics, etc. It can be customized so that certain EPD features can be turned and turned off in countries where data collection of this type is prohibited.

Other advantages may include:
1. Single screen interface—as opposed to 2-4 separate applications with multiple interfaces.
2. Multiple data feeds from multiple EPD sensors—as opposed to a user experience where each screen can only handle one feed at a time.
3. Crowd sourced data inputs from social media—as opposed to just getting one way alerts from an RSS feed or broadcast.
4. Can be used as a public health collection tool in real time—as opposed to collecting data and then sending it a later date in response to an alert.
5. Open API and SDK so that end customers can enhance and extend the software themselves—as opposed to a closed, proprietary, or non-existent SDK or API that forces end users to pay the developing company to extend the capability.

Applications for SNEEZES include:
1. Public health and cohort tracking
2. Public safety
3. Emergency response
4. Intelligence collection
5. Military/law enforcement health and cohort tracking
6. Military sensor planning The term cohort (as used above) effect is used in social science to describe variations in the characteristics of an area of study (such as the incidence of a characteristic or the age at onset) over time among individuals who are defined by some shared temporal experience or common life experience, such as year of birth, or year of exposure to radiation.

The system allows for using multiple applications in parallel and then combining on the server/cloud side.

The present written description uses examples to disclose the present subject matter, including the best mode, and also to enable any person skilled in the art to practice the present subject matter, including making and using any devices or systems and performing any incorporated and/or associated methods. While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

The invention claimed is:

1. A method of controlling a device including a processor operatively coupled to a display, a wireless transceiver and at least one sensor to surreptitiously capture and wirelessly stream audio and/or visual information, the method comprising:
   (a) receiving at least one command input by a user of the device;
   (b) in response to receipt of the at least one command, controlling the device to display a screen that masquerades device operation by concealing the capturing and wirelessly streaming and instead shows a user interactive function that is unrelated to the capturing and wirelessly streaming, and
   (c) wirelessly streaming the captured audio and/or visual information to a server while the screen is displayed, wherein the user interactive function is a function of a user interactive application,
   the displayed screen shows an image comprising data, the displayed data having an appearance that changes automatically and dynamically in real-time, and the at least one sensor comprises a video camera and/or a microphone.

2. The method according to claim 1, wherein the device is a portable handheld wireless device including a handheld housing.

3. The method according to claim 1, wherein the device is a desktop or laptop computer.

4. The method according to claim 1, wherein the at least one sensor comprises a video camera and/or a microphone.

5. The method according to claim 1, wherein the user interactive function is a gambling function of a slot machine game application.

6. The method according to claim 1, wherein the displayed screen shows three or more reels and at least one button.

7. The method according to claim 1, wherein the displayed screen shows "7" and "BAR" symbols.

8. The method according to claim 1, wherein the captured audio and/or visual information is streamed to a server for follow-on analysis and distribution by the server.

9. The method according to claim 1, wherein
the user interactive function is a gambling function of a slot machine game application,
the displayed screen shows an image comprising three or more reels, at least one button, and "7" and "BAR" symbols, and
the at least one sensor comprises a video camera and/or a microphone.

10. A non-transitory computer-readable storage medium having stored therein an information processing program for execution by a device comprising a processor operatively coupled to a display, a wireless transceiver and at least one sensor, the information processing program comprising instructions that, when executed by the processor, causing the device to perform operations including:
receiving at least one command input by a user of the device;
in response to receipt of the at least one command, generating, for display on the display, a screen that masquerades device operation by concealing capturing and wirelessly streaming audio and/or visual information and instead shows a user interactive function that is unrelated to the capturing and wireles sly streaming, and
wireles sly streaming the captured audio and/or visual information to a server while the screen is displayed,
wherein the user interactive function is a function of a user-interactive application, the displayed screen shows an image comprising data, the displayed data having an appearance that changes automatically and dynamically in real-time, and the at least one sensor comprises a video camera and/or a microphone.

11. A device comprising a processor operatively coupled to a display, a wireless transceiver and at least one sensor, the processor being configured to:
receive at least one command input by a user of the device;
in response to receipt of the at least one command, display a screen that masquerades device operation by concealing capturing and wirelessly streaming audio and/or visual information and instead shows a user interactive function that is unrelated to the capturing and wirelessly streaming, and
wirelessly stream the captured audio and/or visual information to a server while the screen is displayed,
wherein the user interactive function is a function of a user-interactive application, the displayed screen shows an image comprising data, the displayed data having an appearance that changes automatically and dynamically in real-time, and the at least one sensor comprises a video camera and/or a microphone.

12. The device according to claim 11, wherein the device is a portable handheld wireless device including a handheld housing.

13. The device according to claim 11, wherein
the user interactive function is a gambling function of a slot machine game application,
the displayed screen shows an image comprising three or more reels, at least one button, and "7" and "BAR" symbols, and
the at least one sensor comprises a video camera and/or a microphone.

14. A system for collecting data from at least one device, the system comprising:
the device according to claim 11; and
a server including a receiver configured to receive the data collected by the at least one sensor of the device, and a processor configured to issue one or more commands to the device to request collecting audio and/or visual information by the at least one sensor of the device.

15. The method according to claim 1, wherein the device is a remote device, and the captured audio and/or visual information can be encrypted on the remote device to maintain privacy and security of both the captured audio and/or visual information and the remote device at rest or in motion.

16. The method according to claim 1, wherein the data includes a number and/or an icon whose appearance changes automatically and dynamically in real time.

17. The method according to claim 1, wherein the user interactive application is a gaming application.

* * * * *